United States Patent
Brilliant et al.

(10) Patent No.: US 10,376,344 B2
(45) Date of Patent: Aug. 13, 2019

(54) IMITATION LIPSTICK WITH CONCEALED TOOTH CLEANING IMPLEMENT

(71) Applicants: Margo Brilliant, Miami, FL (US); Jo Anne Brilliant, Annapolis, MD (US); Robert M. Schwartz, Miami, FL (US)

(72) Inventors: Margo Brilliant, Miami, FL (US); Jo Anne Brilliant, Annapolis, MD (US); Robert M. Schwartz, Miami, FL (US)

(73) Assignee: G and E International LLC, Miami, FL (US)

( * ) Notice: Subject to any disclaimer, the term of this patent is extended or adjusted under 35 U.S.C. 154(b) by 395 days.

(21) Appl. No.: 15/079,471

(22) Filed: Mar. 24, 2016

(65) Prior Publication Data

US 2016/0199162 A1    Jul. 14, 2016

Related U.S. Application Data

(63) Continuation-in-part of application No. 14/621,834, filed on Feb. 13, 2015, now Pat. No. 9,387,058, and a continuation of application No. 13/551,901, filed on Jul. 18, 2012, now Pat. No. 8,973,590.

(60) Provisional application No. 61/508,748, filed on Jul. 18, 2011, provisional application No. 62/207,623, filed on Aug. 20, 2015, provisional application No. 62/168,417, filed on May 29, 2015, provisional application No. 62/138,649, filed on Mar. 26, 2015, provisional application No. 62/244,317, filed on Oct. 21, 2015.

(51) Int. Cl.
| | |
|---|---|
| *A61C 15/02* | (2006.01) |
| *A61C 3/02* | (2006.01) |
| *A45D 40/00* | (2006.01) |

(52) U.S. Cl.
CPC .............. *A61C 15/02* (2013.01); *A61C 3/02* (2013.01); *A45D 40/00* (2013.01)

(58) Field of Classification Search
CPC ............ A61C 15/02; A61C 3/02; A45D 40/00
USPC .............. 206/63.5, 349, 368, 380, 385, 457; 132/309, 321–329; 401/52, 88
See application file for complete search history.

(56) References Cited

U.S. PATENT DOCUMENTS

| | | | |
|---|---|---|---|
| 2,595,403 A | 5/1952 | Neuschaefer | |
| 2,859,754 A | 11/1958 | Futterer | |
| 3,078,856 A | 2/1963 | Bender et al. | |
| 3,310,168 A * | 3/1967 | Landen | A45D 40/04 206/385 |
| 3,802,445 A | 4/1974 | Wesley | |
| 3,991,777 A | 11/1976 | Powers et al. | |
| 4,033,007 A | 7/1977 | Hadary | |
| 4,040,433 A | 8/1977 | Edison | |
| 4,326,548 A * | 4/1982 | Wagner | A61C 15/02 132/328 |

(Continued)

FOREIGN PATENT DOCUMENTS

| | | |
|---|---|---|
| CN | 201123152 | 10/2008 |
| CN | 102038356 B | 7/2012 |

(Continued)

*Primary Examiner* — Luan K Bui
(74) *Attorney, Agent, or Firm* — Robert M. Schwartz; Alfred K. Dassler

(57) ABSTRACT

A tooth cleaning device has a handle portion. An imitation lipstick bullet is disposed on the handle portion. The imitation lipstick bullet has a tooth cleaning implement protruding from an outer surface of the imitation lipstick bullet.

25 Claims, 15 Drawing Sheets

(56) References Cited

U.S. PATENT DOCUMENTS

| | | | |
|---|---|---|---|
| 4,342,324 A | 8/1982 | Sanderson | |
| 4,509,541 A | 4/1985 | Manciocchi, Jr. | |
| 4,800,905 A * | 1/1989 | Stuart | A61C 15/02 132/321 |
| 5,813,421 A * | 9/1998 | Wang | A45D 40/04 132/318 |
| 5,826,998 A * | 10/1998 | Shih | B43K 29/00 401/52 |
| 5,975,901 A * | 11/1999 | Kennedy | A61C 15/02 132/309 |
| 6,082,999 A | 7/2000 | Tcherny et al. | |
| 6,199,695 B1 | 3/2001 | Takeo | |
| 6,234,182 B1 | 5/2001 | Berglund | |
| 6,247,477 B1 * | 6/2001 | Wagner | A45D 44/18 132/309 |
| 6,418,940 B1 | 7/2002 | Tcherny et al. | |
| 6,671,920 B2 | 1/2004 | Pearlman et al. | |
| 2004/0094180 A1 | 5/2004 | Hsu | |
| 2005/0255136 A1 | 11/2005 | Fleissman et al. | |
| 2009/0078280 A1 * | 3/2009 | Fishman | A61C 3/00 132/328 |
| 2010/0078344 A1 * | 4/2010 | Martins | A45D 40/06 206/385 |
| 2011/0070012 A1 * | 3/2011 | Kim | A45D 40/065 401/68 |

FOREIGN PATENT DOCUMENTS

| | | |
|---|---|---|
| JP | 11113930 | 4/1999 |
| JP | 2002253346 | 10/2002 |

* cited by examiner

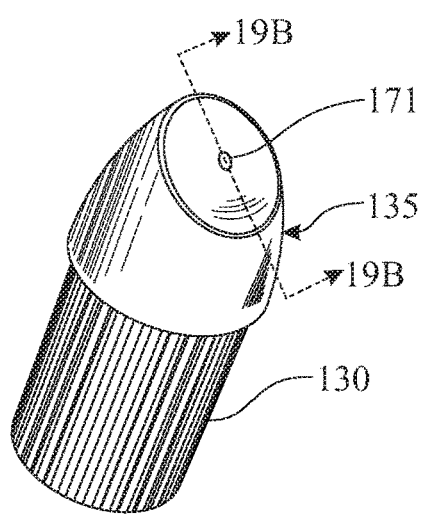
FIG. 18
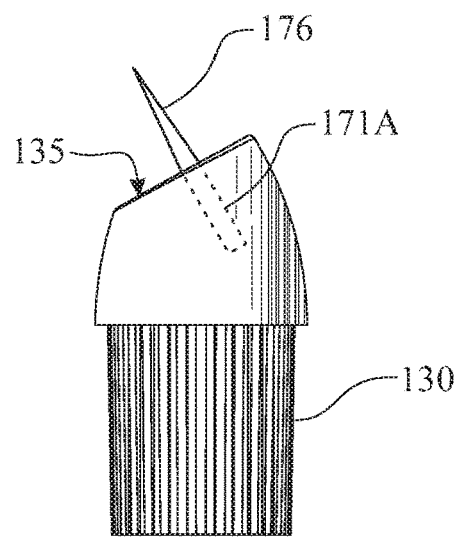
FIG. 19A
FIG. 20
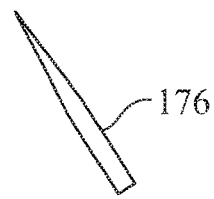
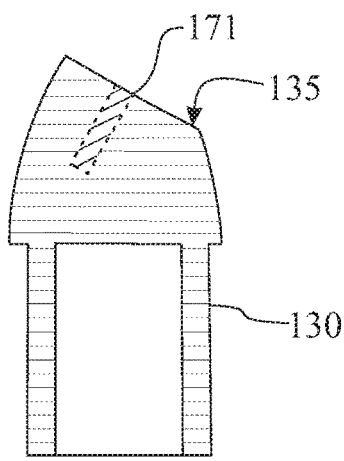
FIG. 19B
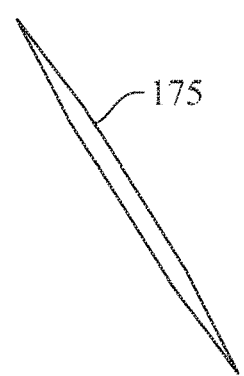
FIG. 21

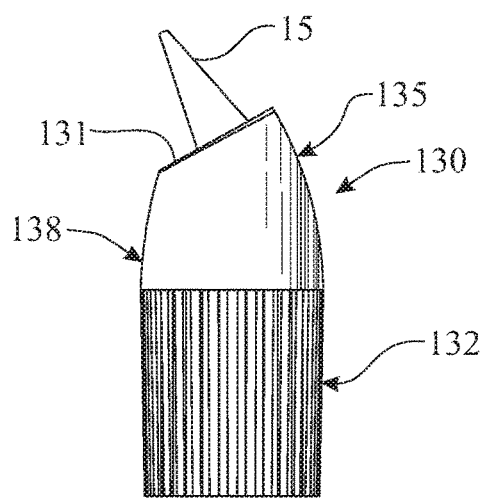# 
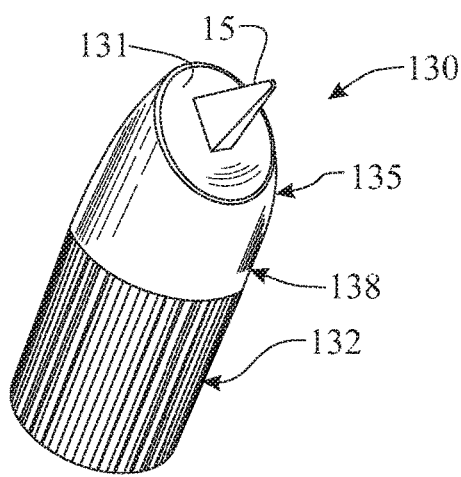
FIG. 25
FIG. 26

IMITATION LIPSTICK WITH CONCEALED TOOTH CLEANING IMPLEMENT

CROSS-REFERENCE TO RELATED APPLICATIONS

This application is a Continuation-in-Part of Co-Pending U.S. patent application Ser. No. 14/621,834, filed Feb. 13, 2015, entitled "Holder for Concealed Tooth Cleaning Implement," which is a Continuation application of U.S. patent application Ser. No. 13/551,901, filed, Jul. 18, 2012, now U.S. Pat. No. 8,973,590, that issued Mar. 10, 2015, entitled "Holder for Concealed Tooth Cleaning Implement", which claimed the benefit of U.S. Provisional Application Ser. No. 61/508,748, filed on Jul. 18, 2011, entitled "Concealed Scalar." This present application also claims the benefit of U.S. Provisional Application Ser. No. 62/244,317, filed Oct. 21, 2015, entitled "Imitation Lipstick With Concealed Tooth Cleaning Implement;" U.S. Provisional Application Ser. No. 62/207,623, filed Aug. 20, 2015, entitled "Imitation Lipstick with Tooth Cleaning Implement;" U.S. Provisional Application Ser. No. 62/168,417, filed May 29, 2015, entitled "Imitation Lipstick with Tooth Cleaning Implement;" and U.S. Provisional Application Ser. No. 62/138,649, filed Mar. 26, 2015, entitled "Lipstick With Concealed Tooth Cleaning Implement." These prior applications are herewith incorporated by reference in their entirety.

BACKGROUND OF THE INVENTION a) Field of the Invention

The invention relates to a tooth cleaning implement for removing particles of food or other debris from teeth of a person or user. The invention also relates to lipstick and lipstick cases.

Description of the Related Art

The present invention is in the art of toothpicks and dental pick devices used as teeth cleaning implements. These implements, when used, are often used in private and out of public view. Toothpicks and dental pick devices are not conducive for use in public or at least at a dinner table. Additionally the invention is in the art of lipstick or lip balm that would be applied to a person's lips; and lipstick cases that hold lipstick that is applied by a user to transfer the lipstick material to the user's lips.

SUMMARY OF THE INVENTION

It is accordingly an object of the invention to provide a tooth cleaning device which overcomes the disadvantages of the heretofore-known devices of this general type and which provides a tooth cleaning device that is inconspicuous and easy to use.

With the foregoing and other objects in view there is provided, in accordance with the invention a tooth cleaning device that has a handle portion. An imitation lipstick bullet is disposed on the handle portion. The imitation lipstick bullet has a tooth cleaning implement protruding from an outer surface of the imitation lipstick bullet.

In accordance with another feature of the invention, the imitation lipstick bullet is replaceably mounted to the handle portion.

In accordance with a further feature of the invention, a cap is removably mounted on the handle portion, the cap conceals the imitation lipstick bullet and the tooth cleaning implement.

In accordance with a further feature of the invention, the tooth cleaning implement and the imitation lipstick bullet are formed of a common material and a common color.

In accordance with an added feature of the invention, the tooth cleaning implement is located on a top portion of the imitation lipstick bullet.

In accordance with an additional feature of the invention the imitation lipstick bullet has a slanted face and the tooth cleaning implement protrudes from the slanted face.

In accordance with another mode of the invention, the tooth cleaning implement has an implement longitudinal axis, the imitation lipstick bullet has a bullet longitudinal axis disposed at an acute angle to the implement longitudinal axis.

In accordance with a further mode of the invention the tooth cleaning implement is disposed on a face of the imitation lipstick bullet, the tooth cleaning implement has a height from the face. The height is less than a diameter of the imitation lipstick bullet below the face.

In accordance with an additional mode of the invention, the outer surface has a surface finish that is the same as a surface finish of a real lipstick bullet.

In accordance with yet another feature of the invention, the handle portion has a guide tube rotationally mounted thereon. The imitation lipstick bullet is extendable into and out of the guide tube.

In accordance with yet a further feature of the invention, the handle portion has a platform disposed inside the guide tube. The bullet is mounted on the platform. The platform is extendable in a direction out of the guide tube and retractable in a direction into the guide tube due to a rotation of the guide tube.

In accordance with yet an added feature of the invention, the imitation lipstick bullet has a bullet mating dimension and the platform has a platform mating dimension. The bullet mating dimension and the platform mating dimension are sized such that there is a slight press fit between the imitation lipstick bullet and the platform.

With the objects of the invention in view, there is also provided a tooth cleaning device includes a handle portion. An imitation lipstick bullet is disposed on the handle portion. The imitation lipstick bullet has a tooth cleaning implement for removing particles of food or other debris from teeth of a person.

In accordance with an additional further mode of the invention a tooth cleaning device includes a imitation lipstick bullet. The imitation lipstick bullet has an outer surface with a pointed protrusion disposed thereon and that protrudes therefrom.

In accordance with yet an additional feature of the invention, the face is orthogonal to a cylinder wall of the imitation lipstick bullet.

In accordance with still another feature of the invention, the tooth cleaning implement is rigid with respect to the imitation lipstick bullet.

In accordance with another mode of the invention, there is a tooth cleaning device for mating with a cup shaped platform of a lipstick case, the tooth cleaning device having a base portion having a cylindrical surface configured and sized for engaging an inner cup surface of the cup shaped platform, a top portion having the appearance of an applicator portion of a real lipstick bullet, the top portion adjoining the base portion, the top portion being larger than said base portion for defining a shoulder between said top portion and said base portion, said shoulder assisting in removal of said tooth cleaning device from said cup-shaped platform.

In accordance with a further mode of the invention, the top portion has an outer surface with a pointed protrusion disposed thereon and protruding therefrom.

In accordance with an additional mode of the invention, the tooth cleaning device is formed of plastic.

In accordance with another mode of the invention, there is a tooth cleaning device for mating with a cup shaped platform of a lipstick case, the tooth cleaning device having a base portion having a cylindrical surface configured and sized for engaging an inner cup surface of the cup shaped platform, a top portion having the appearance of an applicator portion of a real lipstick bullet, and the outer surface has an opening thereon to receive a protrusion within the opening.

In accordance with yet a further mode of the invention, the pointed protrusion is a toothpick, and the opening is sized to mate with the toothpick and hold the toothpick with a friction fit.

Other features which are considered as characteristic for the invention are set forth in the appended claims.

Although the invention is illustrated and described herein as embodied in a tooth cleaning device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 18 is a perspective view of another embodiment of a tooth cleaning device having an internal opening in the outer surface of the imitation lipstick bullet to receive a tooth cleaning implement;

FIG. 19A is a side view of the tooth cleaning device shown in FIG. 18 having a removable tooth cleaning implement;

FIG. 19B is a sectional view of the tooth cleaning device taken along lines 19B-19B in FIG. 18;

FIG. 20 is a plan view of a portion of a toothpick;

FIG. 21 is a plan view of a toothpick;

FIG. 25 is a right side view of an alternate embodiment of the imitation lipstick bullet, the right side view and the left side view are the same; and FIG. 26 is a front perspective view of the alternate embodiment imitation lipstick bullet shown in FIG. 25.

DESCRIPTION OF THE PREFERRED EMBODIMENTS

Figure 1:
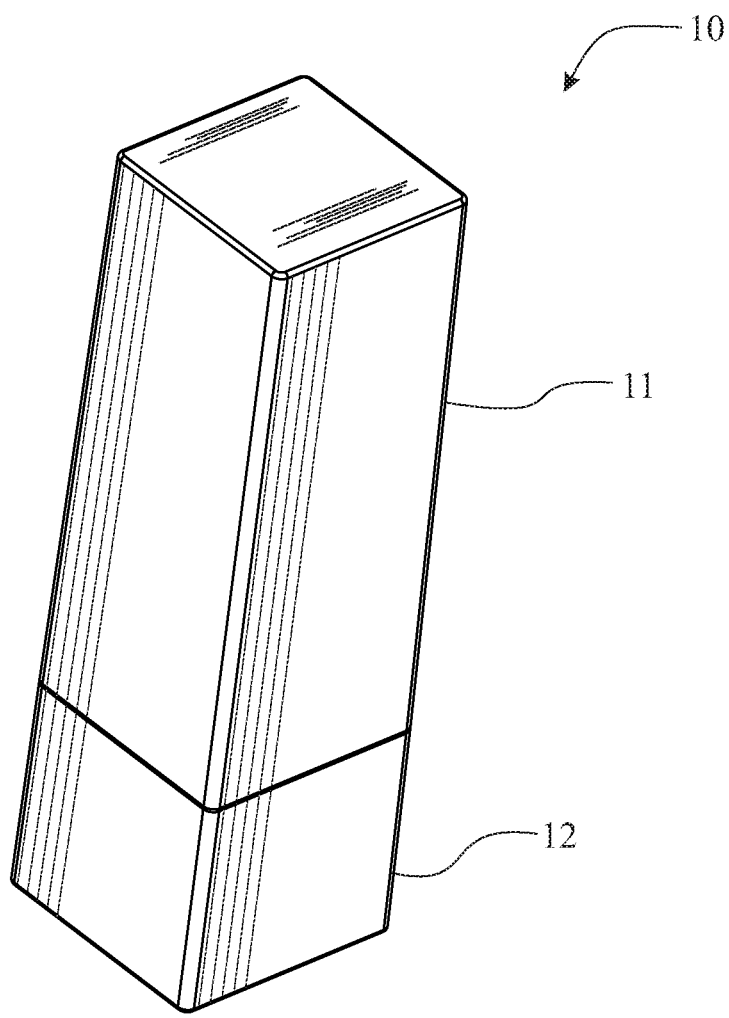
FIG. 1 is perspective view of an outer case of the tooth cleaning implement with a cap in place.

Referring now to the figures of the drawing in detail and first, particularly, to FIGS. 1, 2, 3A and 4A thereof, there is seen an outer case 10 of a tooth cleaning device 1, having a tooth cleaning implement or pick 15. In FIG. 1, the outer case 10 is shown as substantially rectilinear, though the outer case 10 can also be round or any other shape as known in the lipstick industry. The outer case 10 has a cap 11 and a handle/gripping portion 12. The outer case 10 is a holder for an imitation lipstick tube or imitation lipstick bullet 130. The term imitation lipstick bullet serves to define that the imitation lipstick bullet has a shape, size and geometry that resembles a real lipstick bullet for applying lipstick to a user. In this regard, it is noted that real lipstick bullets have various shapes, such as conical, dome, flat top, with or without a slanted surface, and when these real lipstick bullets are used, the lipstick and the color of the lipstick is transferred from the lipstick bullet to the user's lips.

Figure 24:
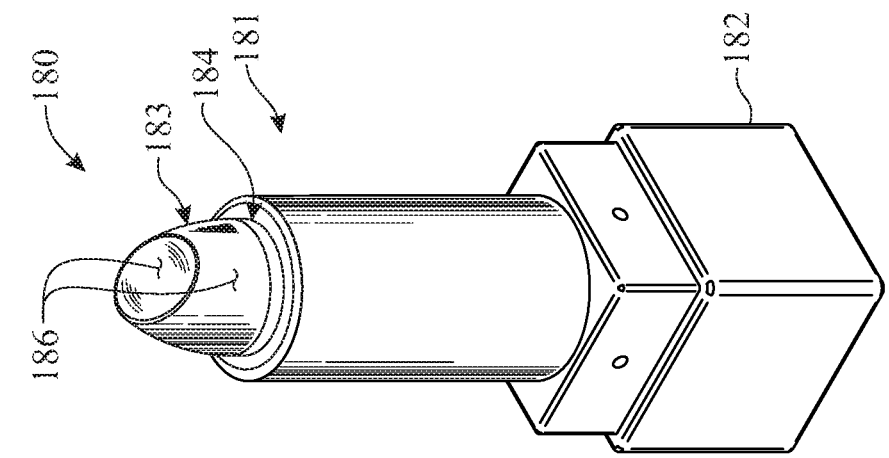
FIG. 24 is a front perspective view of the real lipstick shown in FIGS. 22 and 23.
Figure 23:
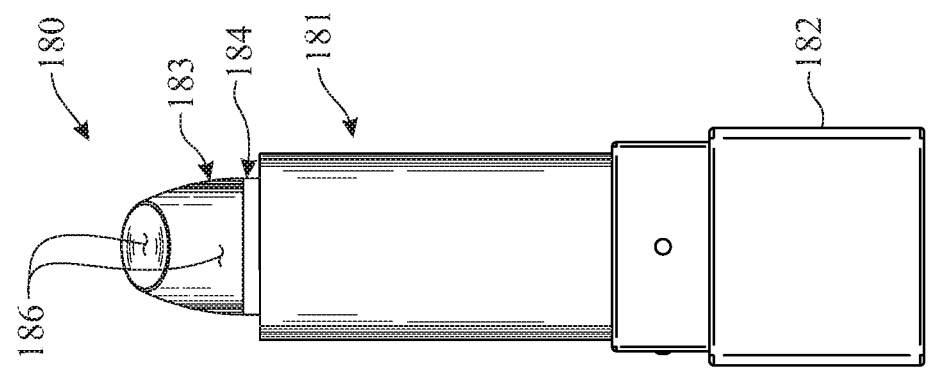
FIG. 23 is a front view of the real lipstick shown in FIG. 22.
Figure 22:
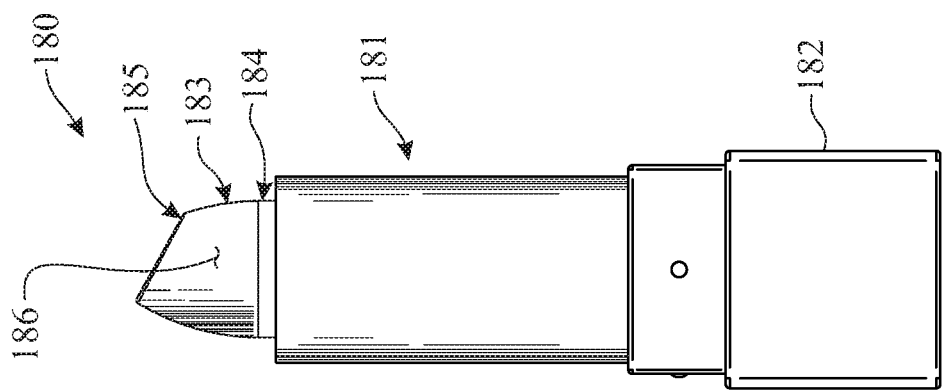
FIG. 22 is a side view of a real lipstick case and real lipstick tube.

FIGS. 22, 23 and 24 show a drawing representation of a typical real lipstick 180, having a lipstick case 181, a handle 182, a real lipstick tube or bullet 183 and a cup shaped portion 184 of a platform that supports the lipstick bullet 183 within lipstick case 181. A removable lipstick cap, not shown, would cover, and protect and conceal the lipstick bullet 183 and fit on the lipstick case 181. Lipstick bullet 183 has a slanted surface 185, though lipstick bullet 183 can have various shapes, such as conical, dome, flat top, with or without a slanted surface. The lipstick bullet 183, when used by a user, transfers the lipstick from the tube of lipstick to the user's lips or other applied area where the lipstick bullet 183 comes in contact with the area to receive the lipstick. The portion of the lipstick tube or bullet 183 that comes in contact with the applied area is referred to herein as the applicator portion 186 of the real lipstick bullet 183. The term applicator portion being any portion of the outer surface of the lipstick bullet 183 that can come in contact with a user to transfer the lipstick to the user.

Figure 12:
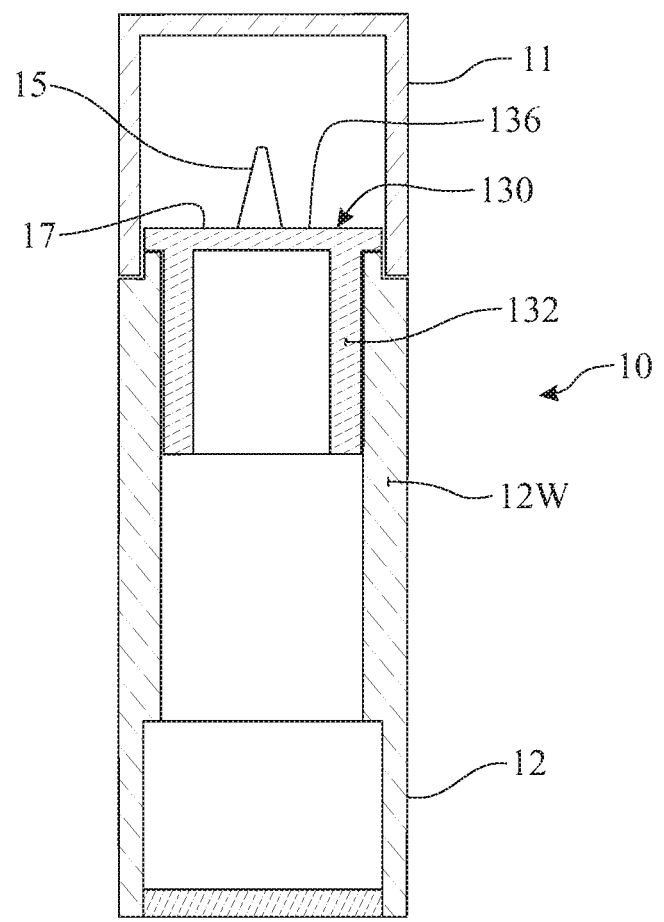
FIG. 12 is a sectional view of another embodiment of a tooth cleaning device having a flat top imitation lip balm bullet, having no internal mechanism and shown with a cap in place.
Figure 16:
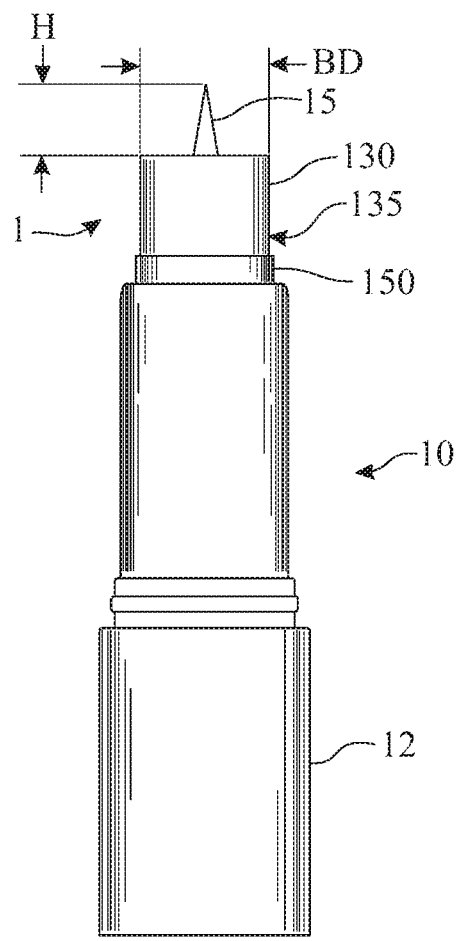
FIG. 16 is front view of another embodiment of a tooth cleaning device with the tooth cleaning implement located on an imitation bullet having a flat top.
Figure 17:
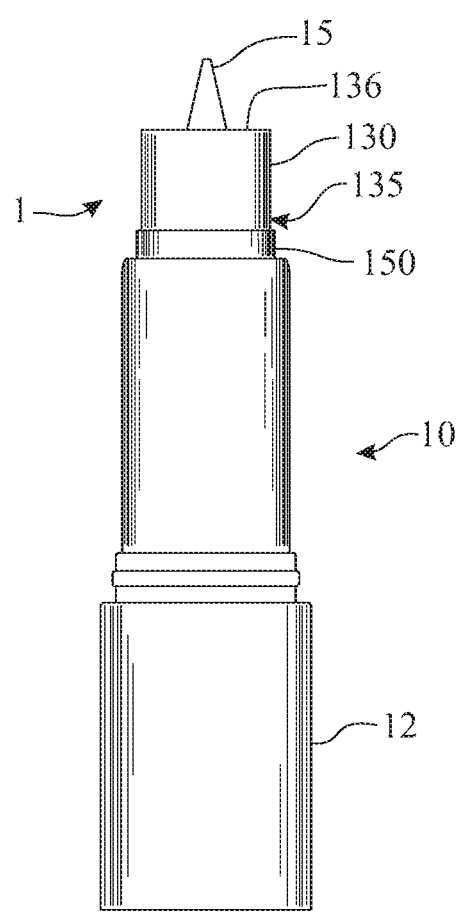
FIG. 17 is side view of the embodiment of a tooth cleaning device in FIG. 16.

Furthermore, the term imitation lipstick bullet 130 as used herein, does not serve to limit color, material such as plastic or rubber as the imitation lipstick bullet 130 can be any color associated with real lipstick and can be of any material that is suitable to serve as a tooth cleaning implement. Additionally, the imitation lipstick bullet 130 is not real lipstick and does not transfer any color/lipstick material to a user's lips. With respect to the instant application, as shown in FIGS. 12, 16 and 17, there is also a possibility for the imitation lipstick bullet to represent a cylindrical imitation lip balm bullet with a flat top surface such as is commonly recognized as Chapstick®, a non-medicated lip balm, and a registered trademark of Wyeth LLC a Delaware company located at 235 East 42nd Street New York, N.Y. 10017.

The imitation lipstick bullet 130 differs in appearance with respect to a real lipstick bullet in that the imitation lipstick bullet 130 includes a pointed protrusion, scaler, tooth cleaning implement, or pick 15 that projects from an outer surface 135 of the imitation lipstick bullet 130. As used herein, the term "pointed protrusion" defines a shape which is not necessarily acute (a sharp point), but includes a rounded tip, a conical tapering with a rounded tip and any other shapes for removing objects from teeth. Likewise, the base of pick 15 can be round or any shape that serves the purpose of a pointed protrusion. The pick 15 defines a portion of a continuous outer surface 135 of the imitation lipstick bullet 130. In other words, in a preferred embodiment there are no seams or crevices between the pick 15 and the remaining outer surface 135 of the imitation lipstick bullet 130 that are subject to allowing a user's saliva and/or particles in the saliva to pass to an interior side of the imitation lipstick bullet 130. This in turn prevents odors from bacteria that would flourish in difficult to clean areas.

The pick 15 in a preferred embodiment is substantially semi-rigid with respect to said imitation lipstick bullet 130. Where "substantially semi-rigid" is understood as having a rigidity that is stiff and solid, but not inflexible such that deflection is permitted of the pick 15 along a height H thereof when applied to pick the user's teeth. The pick 15 can have a rigidity that differs from the rigidity of the outer surface 135 of the lipstick bullet. However, in a preferred embodiment, the pick 15 and the lipstick bullet 130 are formed of a common material and the pick 15 and lipstick bullet 135 are of the same color.

In a preferred embodiment imitation lipstick bullet 130 is made of plastic. As used herein plastic is a material consisting of any of a wide range of synthetic or semi-synthetic organics that are malleable and can be molded into solid objects of diverse shapes.

Figure 3A:
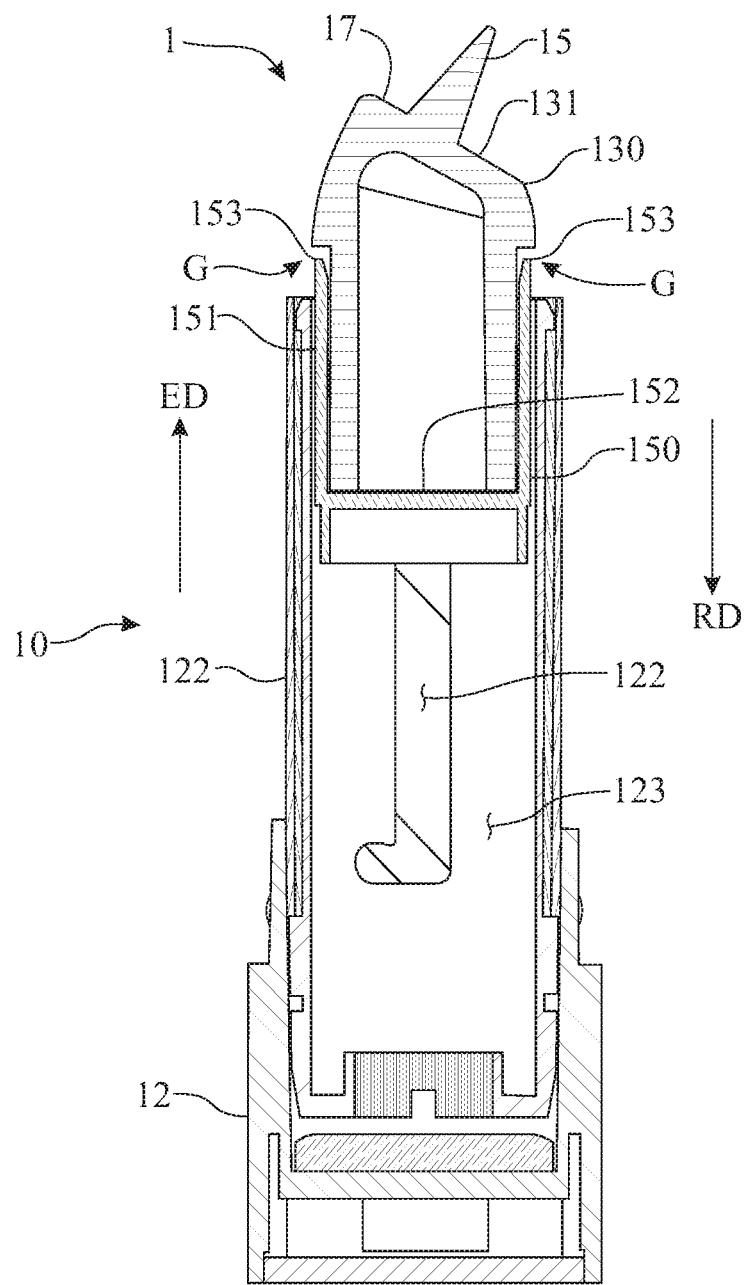
FIG. 3A is a section view of the tooth cleaning implement and imitation lipstick bullet with the cap removed and with the imitation lipstick bullet in an extended working position.
Figure 10:
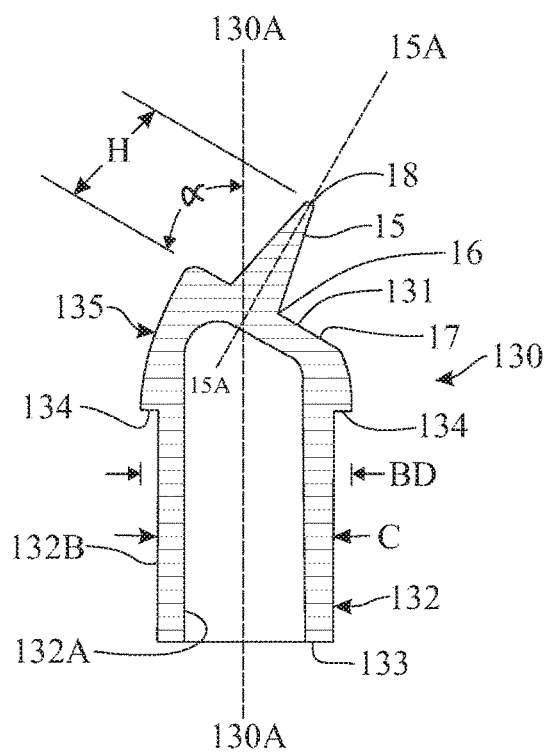
FIG. 10 is a sectional view of the imitation lipstick bullet taken from line A-A in FIG. 6.
Figure 15:
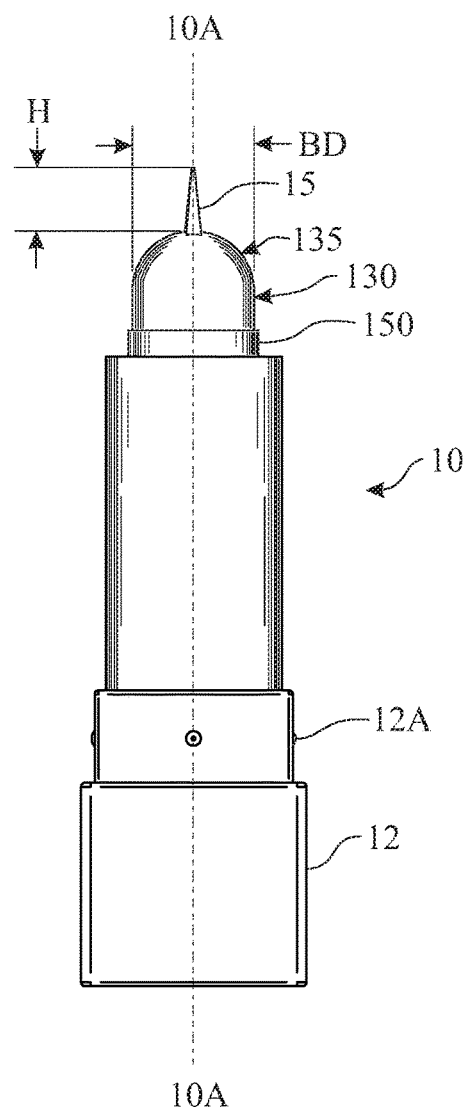
FIG. 15 is front view of the embodiment of a tooth cleaning device shown in FIG. 14.

In FIGS. 3A and 10 the pick 15 is shown projecting from a slanted surface 131 of the imitation lipstick bullet 130. The slanted surface 131 is slanted at an angle α relative to a longitudinal axis 130A of the lipstick bullet 130. The angle α is preferably between 15° and 75°. When the bullet 130 is assembled in the outer case 10, the longitudinal axis 130A is concentric with a longitudinal axis 10A (as shown in FIG. 15) of the outer case 10.

The tooth cleaning implement pick 15 is oriented so that the tooth cleaning implement axis, the center longitudinal axis 15A of the pick 15, as shown in FIG. 10, is substantially orthogonal to the slanted surface 131. Further, the center longitudinal axis 15A of pick 15A is disposed at an acute angle to the longitudinal axis 130A of lipstick bullet 130. However, in the case of an imitation lip balm or a conical or dome shaped lipstick bullet, the pick 15 may project from the outer surface 135 at any position of the imitation lipstick bullet 130.

Figure 2:
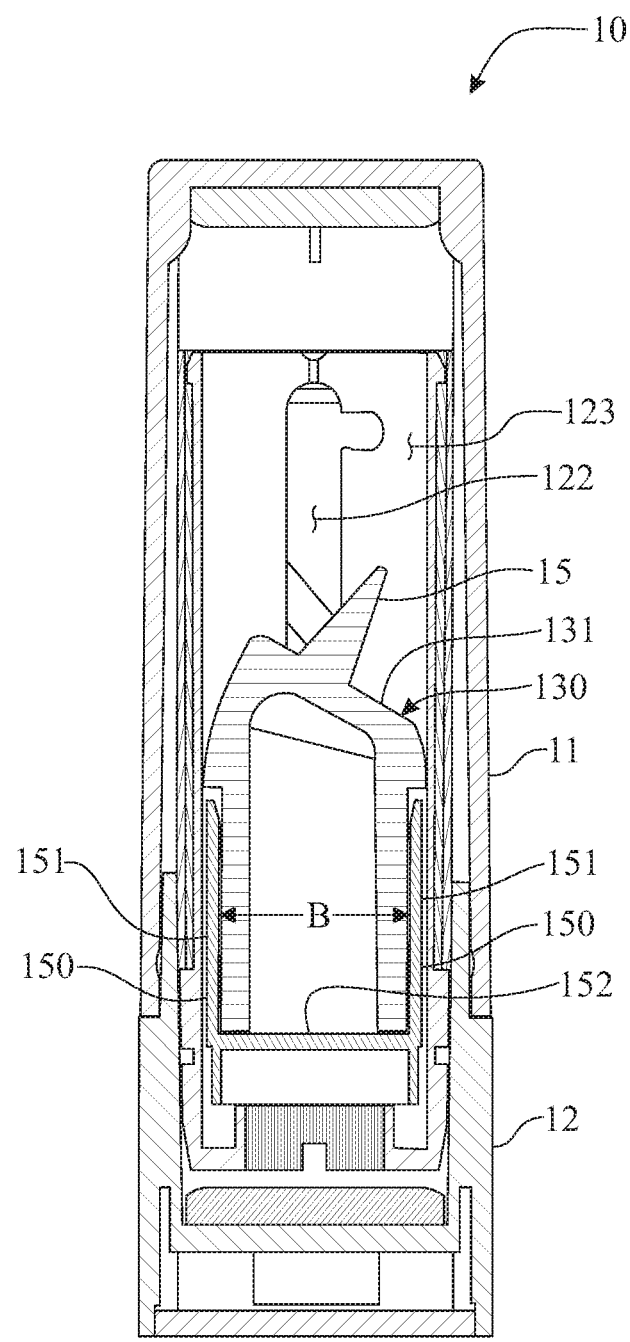
FIG. 2 is an enlarged section view of the tooth cleaning implement with the cap in place and with the imitation lipstick bullet in a retracted storage position.

FIG. 2 shows a handle portion 12 that includes a cup-shaped platform 150 that has a cylindrical platform wall 151. The imitation lipstick bullet 130 has a base cylindrical wall 132, with an inner circumferential surface 132A and an outer circumferential surface 132B. The cylindrical wall 132 has an outer diameter C that mates with an inner diameter B of the cylindrical platform wall 151 of the cup shaped platform 150 when the imitation lipstick bullet 130 is mated with the cup shaped platform 150. The outer surface of the base cylindrical wall 132 has vertical ridges used to align imitation lipstick bullet 130 within cup shaped platform 150.

The mating connection serves to releasably mount the imitation lipstick bullet 130 to the cup shaped platform 150. The mating connection may be a threaded connection, bayonet connection, or a slight press fit. With respect to the present invention, a slight press fit represents a fit which is loose enough to allow the imitation lipstick bullet 130 to be inserted and removed by hand to the cup shaped platform 150 without requiring any additional tools, while being sufficiently tight so that the imitation lipstick bullet 130 does not separate from the cup shaped platform 150 due to orientation of the outer case 10 or handle portion 12 (upside down position of the handle portion 12) or due to transport handling of the outer case 10 in a user's purse (i.e. jarring or jostling that may occur while the user carries the outer case 10).

Figure 3B:
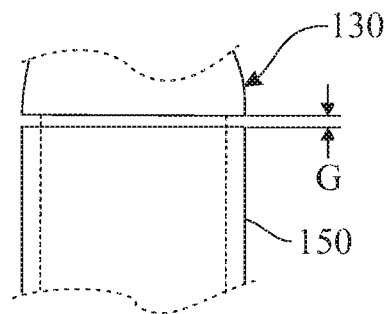
FIG. 3B is a partial enlarged side view of the imitation lipstick bullet and the cup shaped platform in the outer case.
Figure 3C:
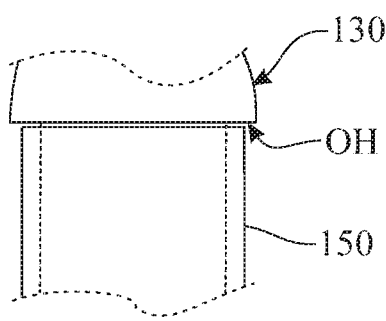
FIG. 3C is a partial enlarged side view of another embodiment of the imitation lipstick bullet and the cup shaped platform in the outer case.
Figure 5:
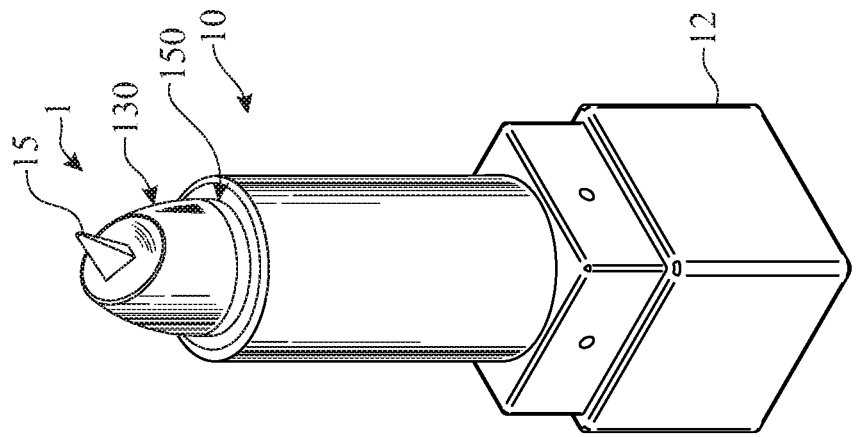
FIG. 5 is perspective view of the tooth cleaning implement in an outer case with the cap removed and with the imitation lipstick bullet in an extended working position.
Figure 4B:
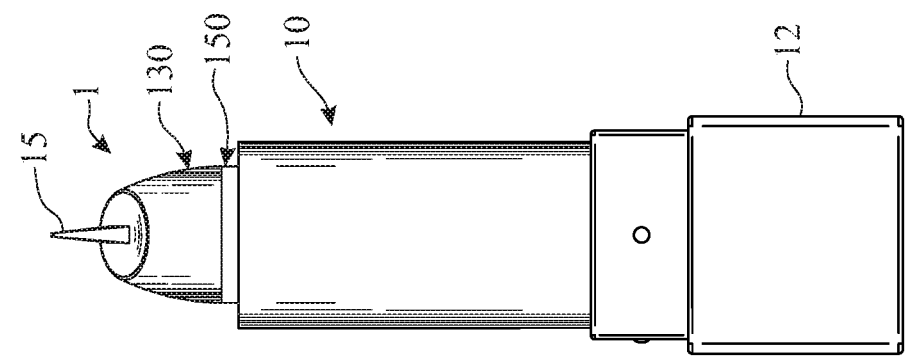
FIG. 4B is a front view of the tooth cleaning implement in an outer case with the cap removed and with the imitation lipstick bullet in an extended working position.
Figure 4A:
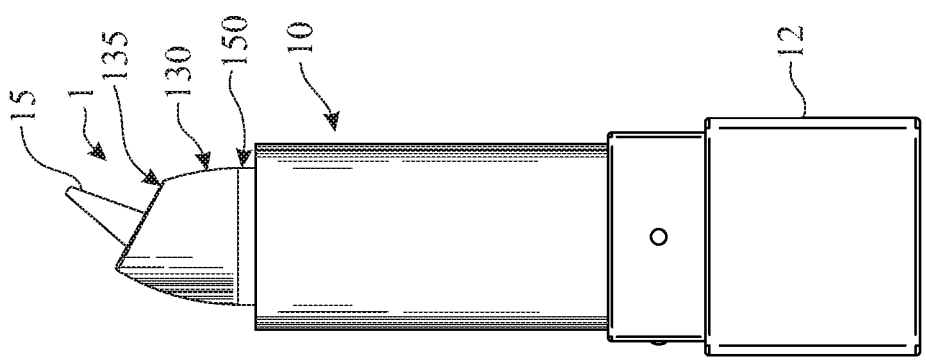
FIG. 4A is a side view of the tooth cleaning implement in an outer case with the cap removed and with the imitation lipstick bullet in an extended working position.
Figure 6:
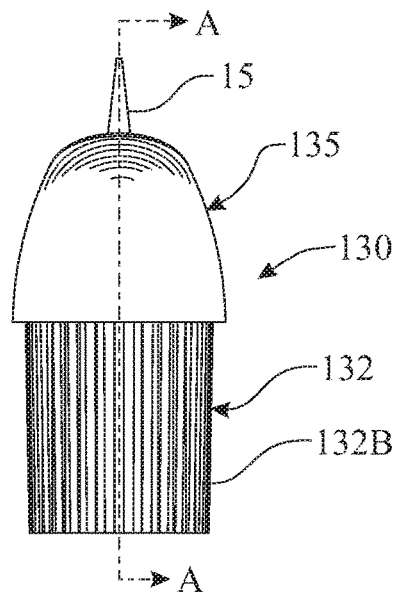
FIG. 6 is a rear view of the imitation lipstick bullet insert shown without an outer case.
Figure 7:
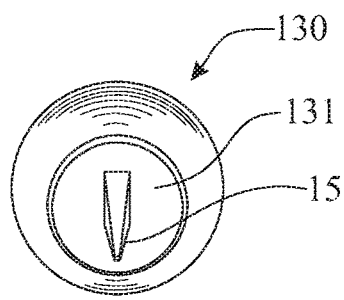
FIG. 7 is a top view of the imitation lipstick bullet.
Figure 8:
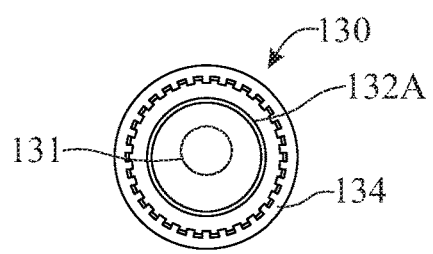
FIG. 8 is a bottom view of the imitation lipstick bullet.
Figure 9A:
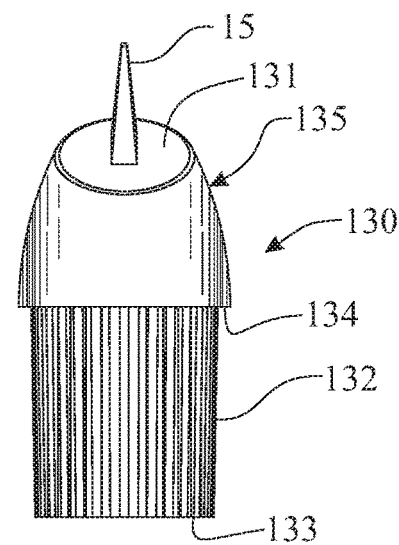
FIG. 9A is a front view of the imitation lipstick bullet.
Figure 9B:
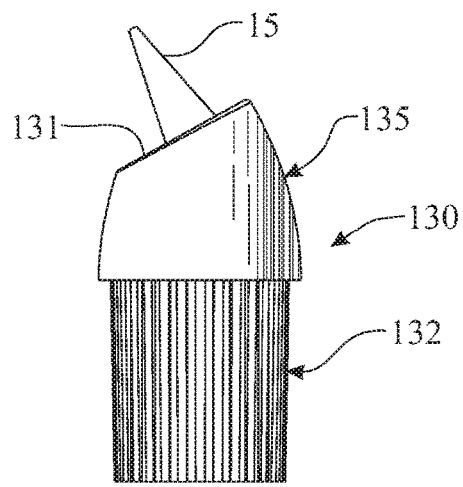
FIG. 9B is a right side view of the imitation lipstick bullet, the right side view and the left side view are the same view.
Figure 9C:
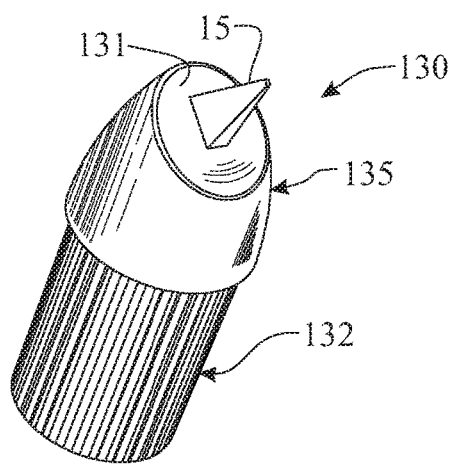
FIG. 9C is a front perspective view of the imitation lipstick bullet.

As shown in FIG. 2, the cup shaped platform 150 has a support surface 152 which faces the lipstick bullet 130. The cylindrical wall 132 of imitation lipstick bullet 130 has a base surface 133 that rests against or is in close proximity to the support surface 152 when the imitation lipstick bullet 130 is mated with the platform 150. The imitation lipstick bullet 130 is provided with a shoulder 134 on the cylindrical wall 132. The shoulder 134 is disposed at a distance from the base surface 133 that is greater than a distance from the support surface 152 to a rim 153 of the cylindrical platform wall 151 so that a slight gap G is provided between the rim 153 of the platform wall 151 and the shoulder 134. As shown in enlarged view FIG. 3B, the gap G allows a user to insert a fingernail into the gap G and initiate the removal of the imitation lipstick bullet 130 from the platform 150 when the imitation lipstick bullet 130 is in the extended position. As shown in FIG. 3C, it is also possible for the shoulder 134 to extend beyond the platform wall 151 to provide an overhang OH. It is also possible to provide the overhang OH with the gap G to better facilitate removal of the lipstick bullet 130.

Figure 13:
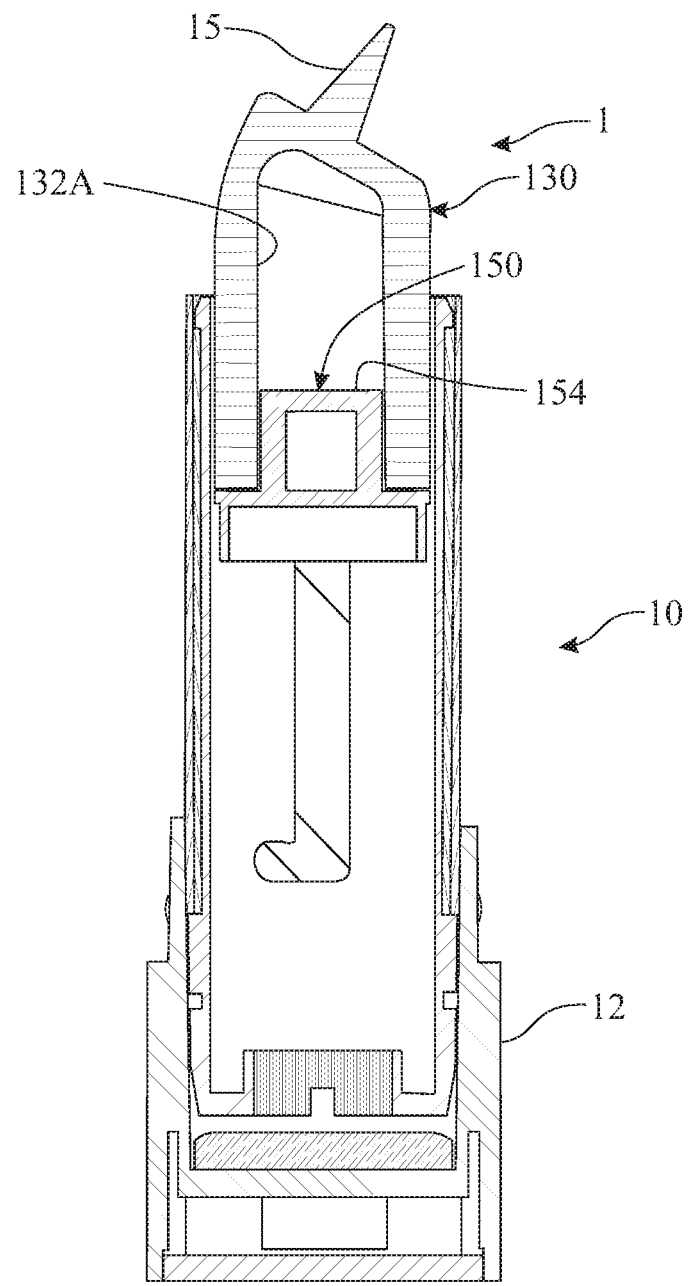
FIG. 13 is a sectional view of another embodiment of a tooth cleaning device with the imitation lipstick bullet having an alternate attachment to the lipstick case, the cap is not shown.

As is shown in FIG. 13 it is possible to reverse the outside diameter and the inside diameter between the imitation lipstick bullet 130 and the platform 150. Specifically the platform 150 has a male projection 154 with an outside diameter that mates with an inside diameter of the inner surface 132A of the imitation lipstick bullet 130. The connection can be of the same types mentioned above with respect to FIG. 2 (slight press fit, threaded connection, or bayonet connection).

As shown in FIG. 2, the handle portion 12 includes a guide tube 122 that is rotatably mounted with respect to the handle portion 12. The guide tube 122 is provided with an internal guide sleeve 123 in which the platform 150 is disposed. The guide sleeve 123 is rotational fixed to the handle portion 12 and rotates relative to the guide tube 122, along with the handle portion 12. The guide sleeve 123 is provided with a linear groove that extends along a longitudinal axis of the outer case 10 and the guide tube 122 has a spiral groove that winds around the guide tube 122 while rising along the longitudinal axis 10A of the case 10. The platform 150 has a fixed projection that extends into the linear groove and into the spiral groove. Accordingly, during a rotation of handle portion 12 relative to the guide tube 122, the fixed projection moves along the linear groove and the spiral grove rotates relative to the cup shaped platform 150 and the fixed projection causes the platform 150 to move along the guide tube 122 in an extension direction ED or a retraction direction RD. Such an extension/retraction is common to what is used in lipstick cases, as known in the art, with an extendable and retractable real lipstick bullet in a lipstick case. The above, is merely one option for extending and retracting a lipstick bullet. Other types of retraction/extension mechanisms are possible and within the scope of the invention.

Furthermore, extension/retraction of the platform 150 results in the imitation lipstick bullet 130 extending out of the guide tube 122 into a use position for using the pick 15 on a user's teeth and retracting the imitation lipstick bullet 130 back into the guide tube 122, where the imitation lipstick bullet 130 and the pick 15 are protected inside the guide tube 122. When in the extended position, at least an exposed portion of the imitation lipstick bullet 130 that is outside of the guide tube 122 has an outer surface 135. The outer surface 135 has a surface finish that is the same as or substantially similar to a surface finish of an actual or real lipstick bullet. The surface finish helps to conceal or hide the fact that the imitation lipstick bullet 130 is actually provided for cleaning objects from between a user's teeth.

The handle 12 has small projections 12A that fit a corresponding detent (not shown) on the inside of cap 11, to secure cap 11 on handle 12.

Pick 15 has a height H from the support surface of the imitation lipstick bullet 130. Referring to FIG. 10, the height H of pick 15 is from base 16 at a face 17 of the imitation lipstick bullet 130 to the end or tip 18 of the pick 15. The height H of pick 15 is less than the bullet diameter BD of the exposed portion of the imitation lipstick bullet 130 (i.e. the diameter is at the portion of the imitation lipstick bullet 130 that is below the face 17 from which the pick 15 protrudes), where the face 17 is the portion of the imitation lipstick bullet 130 which resembles an actual or real lipstick bullet. For example, in FIG. 3A face 17 would be at slanted surface 131, in FIG. 12, face 17 would be at flat head 136, and in FIGS. 14 and 15 face 17 would be at the widest portion of the spherical shape surface 137. It is noted that when considering a square lipstick bullet the diameter pertains to the dimension from corner to corner (i.e. the diagonal of the cross section). This dimensional feature helps to further conceal the pick 15 and the fact that the user is using a tooth cleaning device and is not applying lipstick, though it is meant to look like the user is applying lipstick.

FIG. 3A shows the imitation lipstick bullet 130 in an extended position, with the pick 15 available to clean a user's teeth. The platform 150 has been moved in the extension direction ED by a rotation of the handle portion 12 relative to the guide tube 122. As shown in FIG. 3A, the gap G is above the rim 153 in the extended position. The gap G is available to provide access to a user, e.g. the user's fingernail to pull and then remove the imitation lipstick bullet 130 from the platform 150, to facilitate cleaning and replacement of the imitation lipstick bullet 130. A user would remove the imitation lipstick bullet 130 to clean the lipstick bullet 130 after use of the tooth cleaning implement, for example when at home after use at a dinner. The user would then re-insert the lipstick bullet 130 after cleaning. Alternatively, a user may have a replacement lipstick bullet 130 that would be used to replace a previously used lipstick bullet 130 that had been disposed. Thus another aspect of the present invention is to provide a source of imitation lipstick bullets 130 for use as replacements of the lipstick bullet 130.

Figure 11:
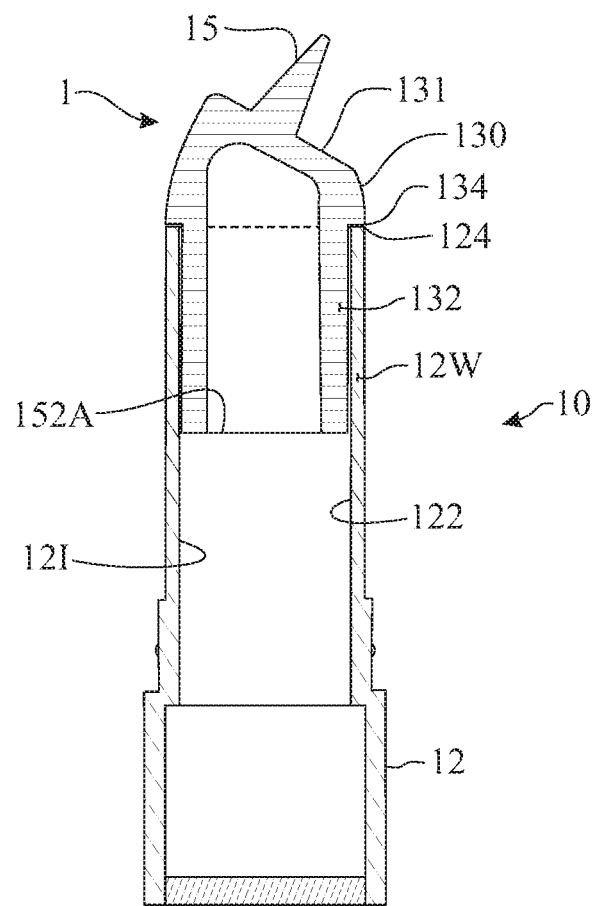
FIG. 11 is a sectional view of another embodiment of a tooth cleaning device having a lipstick bullet with an outer case having no internal mechanism and the cap is not shown.

FIG. 11 shows an embodiment where the imitation lipstick bullet 130 is not disposed on a cup shaped platform 150. Instead, the handle portion 12 has a tubular wall 12W that has an inner diameter 121 that receives the outer circumferential surface 132B of the cylindrical wall 132 of the imitation lipstick bullet 130. The mating of the imitation lipstick bullet 130 with the tubular wall 12W is with a slight press fit, in the same manner as previously disclosed with respect to the slight press fit between the imitation lipstick bullet 130 and the cup shaped platform 150. The shoulder 134 of the imitation lipstick bullet 130 rests against a rim 124 of the wall 12W. The inside diameter 121 of the wall 12W may be provided with a shoulder 152A against which the base surface 133 of the imitation lipstick bullet 130 rests against. The longitudinal position of the shoulder 152A on the wall 12W is such that the shoulder 134 of the imitation lipstick bullet 130 is separated from the rim 124 of the wall 12W to create a gap (gap G as noted above with respect to FIG. 3B), which helps facilitate removal of the imitation lipstick bullet 130. It is also possible to have the overhang OH as shown in FIG. 3C.

Alternatively, it is possible for the mated connection between the platform 150 and the imitation lipstick bullet 130 to be made by a threaded connection or a bayonet type connection. The embodiment of FIG. 11 therefore removes the retraction and extension capabilities of the device and provides a simpler construction. On the other hand this removes the feature of being used in the manner of real lipstick, which some users may prefer.

It is possible for the wall portion 12W of the handle 12 to be dimensioned to engage the inside diameter of the imitation lipstick bullet 130 and for the imitation lipstick bullet 130 to be mated to the handle 12 with one of the connections discussed above.

FIG. 12 shows an embodiment where the imitation lipstick bullet 130 corresponds to an imitation lip balm bullet 130 with a flat head 136. The fit of the imitation lipstick bullet 130 is as discussed above with respect to FIG. 11. Furthermore, the handle 12 has a collar about an outside diameter of the handle 12 which is closer to the rim of the wall 12W in order to accommodate a cap 11 which resembles a cap of a lip balm container. Embodiments with an imitation lipstick bullet 130 with a flat top 136 having a pick 15 extending therefrom are also shown in FIGS. 16 and 17.

Figure 14:
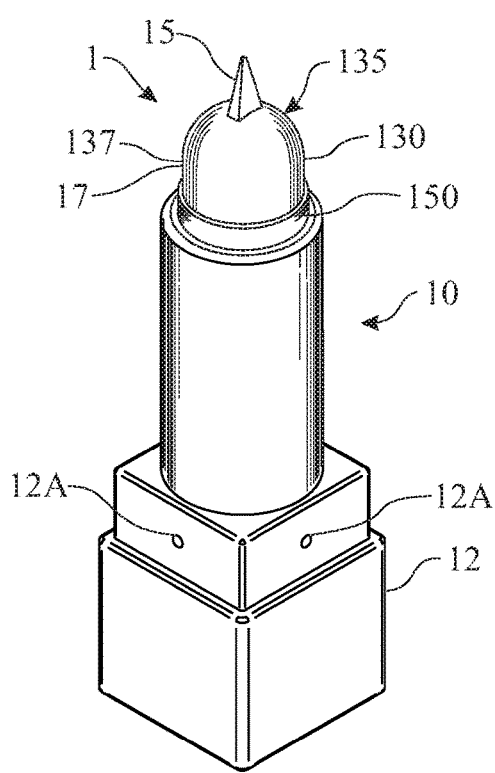
FIG. 14 is front perspective view of another embodiment of a tooth cleaning device having an imitation lipstick bullet with a spherical shape, the cap is not shown.

FIGS. 14 and 15 show an alternate embodiment of the lipstick bullet 130 having a substantially spherical shaped surface 137, with the pick 15 orientated at the top of the spherical shaped bullet 130. Pick 15 is orientated along the longitudinal axis 10A of lipstick case 10.

Another embodiment of the tooth cleaning device 1 of the present invention is shown in FIG. 18 where the imitation lipstick bullet 130, is without an integral tooth cleaning implement protruding from the outer surface 135 of the lipstick bullet 130. In this embodiment imitation lipstick bullet 130, has a cylindrical hole 171A having an opening 171 on the outer surface 135, to receive a tooth cleaning implement such as a toothpick 175 or a portion of a toothpick 176. The cylindrical hole 171A has a round cross section and opening 171 is round, however, the hole 171A and opening 171 can be of other shapes and sizes including rectangular, triangular, star shaped or in any other shape or cross section. In this manner, a user can insert a tooth cleaning implement, such as a portion of a toothpick 176, through the opening 171 into hole 171A of the lipstick bullet 130. Hole 171A is sized to securely hold a toothpick there within. The toothpick 176 would have a friction fit within hole 171A such that the outer portions of toothpick 176 or any other tooth cleaning implement would fit securely against the inner wall of hole 171A. Other mating connections as mentioned above with respect to FIG. 2 (slight press fit, threaded connection, or bayonet connection) may be used as well. The manner of use is substantially the same, in that the lipstick bullet 130 would be held in place and disguised in use as heretofore described in any of the outer cases 10 heretofore described. Further the hole 171A and opening 171 are used as an alternative to the protruding pick 15 in any of the other shaped embodiments heretofore described.

FIGS. 25 and 26 show an alternate embodiment of lipstick bullet 130 where the diameter of the top portion 138 of imitation lipstick bullet 130 is the same as the diameter of the base portion, at the cylinder wall 132 where the two adjoin.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

We claim:

1. A tooth cleaning device comprising:
a handle portion;
an imitation lipstick bullet disposed on said handle portion, said imitation lipstick bullet having a tooth cleaning implement protruding from an outer surface of said imitation lipstick bullet; and
said handle portion having a guide tube rotationally mounted thereon, said imitation lipstick bullet being extendable into and out of said guide tube.

2. The tooth cleaning device according to claim 1, wherein said imitation lipstick bullet is replaceably mounted to said handle portion.

3. The tooth cleaning device according to claim 1, further comprising a cap removably mounted on said handle portion, said cap concealing said imitation lipstick bullet and said tooth cleaning implement.

4. The tooth cleaning device according to claim 1, wherein said tooth cleaning implement and said imitation lipstick bullet are formed of a same material.

5. The tooth cleaning device according to claim 1, wherein said imitation lipstick bullet has a slanted face and said tooth cleaning implement protrudes from said slanted face.

6. The tooth cleaning device according to claim 1, wherein said tooth cleaning implement has an implement longitudinal axis, said imitation lipstick bullet has a bullet longitudinal axis disposed at an acute angle to said implement longitudinal axis.

7. The tooth cleaning device according to claim 1, wherein said tooth cleaning implement is disposed on a face of said imitation lipstick bullet, said tooth cleaning implement has a height from said face, the height is less than a diameter of said imitation lipstick bullet below said face.

8. The tooth cleaning device according to claim 1, wherein said outer surface has a surface finish that is the same as a surface finish of real lipstick bullet.

9. The tooth cleaning device according to claim 1, wherein said handle portion has a platform disposed inside said guide tube, said imitation lipstick bullet is mounted on said platform, said platform is extendable in a direction out of said guide tube and retractable in a direction into said guide tube due to a rotation of said guide tube.

10. The tooth cleaning device according to claim 9, wherein said imitation lipstick bullet has a bullet mating dimension and said platform has a platform mating dimension, said bullet mating dimension and said platform mating dimension are sized such that there is a slight press fit between the imitation lipstick bullet and said platform.

11. The tooth cleaning device according to claim 1, wherein said tooth cleaning implement is semi-rigid with respect to said imitation lipstick bullet.

12. The tooth cleaning device according to claim 1, wherein said tooth cleaning implement and said imitation lipstick bullet are formed of a common color.

13. A tooth cleaning device comprising:
a handle portion;
an imitation lipstick bullet disposed on said handle portion, said imitation lipstick bullet having a tooth cleaning implement for removing particles of food or other debris from the teeth of a person; and
said handle portion having a guide tube rotationally mounted thereon, said imitation lipstick bullet being extendable into and out of said guide tube.

14. The tooth cleaning device according to claim 13, wherein said tooth cleaning implement is disposed on a face of said imitation lipstick bullet, said tooth cleaning implement has a height from said face, the height is less than a diameter of said imitation lipstick bullet below said face.

15. The tooth cleaning device according to claim 13, wherein said imitation lipstick bullet has an outer surface with a surface finish that is the same as a surface finish of a real lipstick bullet.

16. The tooth cleaning device according to claim 13, wherein said handle portion has a platform disposed inside said guide tube, said bullet is mounted on said platform, said platform is extendable in a direction out of said guide tube and retractable in a direction into said guide tube due to a rotation of said guide tube.

17. The tooth cleaning device according to claim 16, wherein said imitation lipstick bullet has a bullet mating dimension and said platform has a platform mating dimension, said bullet mating dimension and said platform mating dimension are sized such that there is a slight press fit between the imitation lipstick bullet and said platform.

18. The tooth cleaning device according to claim 13, wherein said tooth cleaning implement is semi-rigid with respect to said imitation lipstick bullet.

19. The tooth cleaning device according to claim 13, wherein said tooth cleaning implement and said imitation lipstick bullet are formed of a common color.

20. A tooth cleaning device comprising:
a handle portion;
an imitation lipstick bullet disposed on said handle portion, said imitation lipstick bullet having an outer surface having a pointed protrusion disposed thereon and protruding therefrom; and
said handle portion having a guide tube rotationally mounted thereon, said imitation lipstick bullet being extendable into and out of said guide tube.

21. The tooth cleaning device according to claim 20, wherein said outer surface includes a slanted surface, said pointed protrusion is disposed on said slanted surface.

22. The tooth cleaning device according to claim 20, wherein said pointed protrusion is disposed on a face of said imitation lipstick bullet defining an outer surface of said imitation lipstick bullet, said pointed protrusion has a height from said face, the height is less than a diameter of said imitation lipstick bullet below said face.

23. The tooth cleaning device according to claim 22, wherein said face is orthogonal to said outer surface of said imitation lipstick bullet.

24. The tooth cleaning device according to claim 20, wherein said outer surface has a surface finish that is the same as a surface finish of a real lipstick bullet.

25. The tooth cleaning device according to claim 20, wherein said pointed protrusion is semi-rigid with respect to said imitation lipstick bullet.

\* \* \* \* \*